(12) United States Patent
Li et al.

(10) Patent No.: US 10,941,120 B1
(45) Date of Patent: Mar. 9, 2021

(54) 6-AMINOURACIL CASSIC ACID ESTER WITH ANTIBACTERIAL ACTIVITY AND A METHOD OF PREPARING THE SAME

(71) Applicants: Han Li, Xi'an (CN); Nan Hui, Xi'an (CN); Chengyuan Liang, Xi'an (CN); Xingke Ju, Xi'an (CN); Guaiping Qiao, Xi'an (CN); Juan Li, Xi'an (CN); Yuanyuan He, Xi'an (CN); Bin Tian, Xi'an (CN); Yongbo Wang, Xi'an (CN); Jingwen Xu, Xi'an (CN); Liang Qi, Xi'an (CN); Dan Yang, Xi'an (CN); Qianqian Zhao, Xi'an (CN); Yanjun Li, Xi'an (CN); Qiao Zeng, Xi'an (CN); Gennian Mao, Xi'an (CN); Limei Wang, Xi'an (CN)

(72) Inventors: Han Li, Xi'an (CN); Nan Hui, Xi'an (CN); Chengyuan Liang, Xi'an (CN); Xingke Ju, Xi'an (CN); Guaiping Qiao, Xi'an (CN); Juan Li, Xi'an (CN); Yuanyuan He, Xi'an (CN); Bin Tian, Xi'an (CN); Yongbo Wang, Xi'an (CN); Jingwen Xu, Xi'an (CN); Liang Qi, Xi'an (CN); Dan Yang, Xi'an (CN); Qianqian Zhao, Xi'an (CN); Yanjun Li, Xi'an (CN); Qiao Zeng, Xi'an (CN); Gennian Mao, Xi'an (CN); Limei Wang, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 16/909,862

(22) Filed: Jun. 23, 2020

(51) Int. Cl.
*C07D 239/545* (2006.01)

(52) U.S. Cl.
CPC .............. *C07D 239/545* (2013.01)

(58) Field of Classification Search
CPC ................................. C07D 239/545
See application file for complete search history.

(56) References Cited

FOREIGN PATENT DOCUMENTS

CN 105884645 B * 8/2016

OTHER PUBLICATIONS

CN 105884645—Rhein Type Compound and Purpose thereof, Machine Translation, 19 pages (2016).*
PubChem CID 4451350, Create Date: Sep. 15, 2005.*

* cited by examiner

*Primary Examiner* — Deepak R Rao

(57) ABSTRACT

A compound having the formula (I):

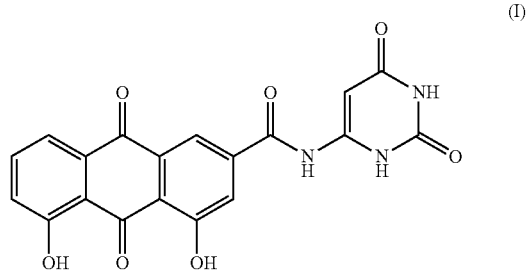

is disclosed. A method of preparing the compound of formula (I) is also disclosed.

15 Claims, 2 Drawing Sheets

6-AMINOURACIL CASSIC ACID ESTER WITH ANTIBACTERIAL ACTIVITY AND A METHOD OF PREPARING THE SAME

FIELD OF THE INVENTION

The present invention relates to the field of medicinal chemistry, in particular, to a 6-aminouracil cassic acid ester with antibacterial activity and a method of preparing the same.

BACKGROUND OF THE INVENTION

With the widespread use of antibiotics, the overuse of antibiotics is becoming more common. Microorganisms that develop tolerance to corresponding antibiotics have emerged, posing a new threat to human health. The emergence of drug-resistant bacteria increases the difficulty of curing infectious diseases. Both Gram-positive bacteria and Gram-negative bacteria have the trend of drug resistance, and the problem of drug resistance of Gram-positive bacteria is more serious. Methicillin-resistant *Staphylococcus aureus* is a common and highly toxic bacteria in clinic. Since its discovery, it has spread almost all over the world, and it is a very thorny problem in clinical anti-infective treatment. It is urgent to develop new antimicrobials, and many pharmaceutical companies in the world are actively looking for new drugs that can deal with multidrug-resistant bacteria. Modifying the chemical structure of existing antimicrobials under the guidance of structure-activity relationship is a common method to develop new drugs for drug-resistant bacteria.

Cassic acid (also known as rhein) is a natural anthraquinone compound (compound of formula II), which has a variety of biological and pharmacological activities and can be extracted from rhubarb. It has many effects, such as improving glucose and lipid metabolism, protecting liver, anti-fibrosis, anti-oxidation, anti-inflammation, antibacterial, anti-cancer and anti-tumor. However, its clinical application is limited to a great extent because of its poor water solubility and low bioavailability.

6-Aminouracil (compound of formula III) is used in the synthesis of pharmaceutical products. For example, it is used as an intermediate for caffeine, theophylline, SDM etc.

In the present invention, cassic acid is modified by the 6-aminouracil structure to obtain a 6-aminouracil cassic acid ester. Preliminary antibacterial activity experiment shows that the compound has excellent antibacterial activity and has high medical research and application value in the treatment of infectious diseases caused by multidrug resistant bacteria.

SUMMARY OF THE INVENTION

In one embodiment, the present invention provides a compound having formula (I) (6-aminouracil cassic acid ester).

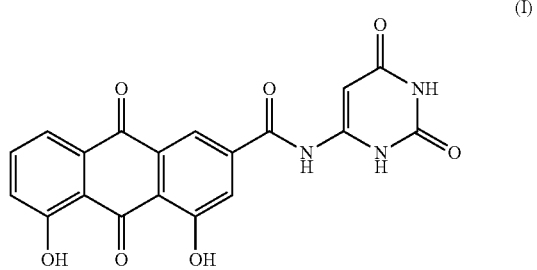 [SMILES: O=C(Nc1cc(=O)[nH]c(=O)[nH]1)c1cc(O)c2c(c1)C(=O)c1cccc(O)c1C2=O]

In another embodiment, the present invention provides a method of preparing the compound of formula (I). The method includes reacting the compound of formula (II) with the compound of formula (III) in organic solvent to obtain the compound of formula (I):

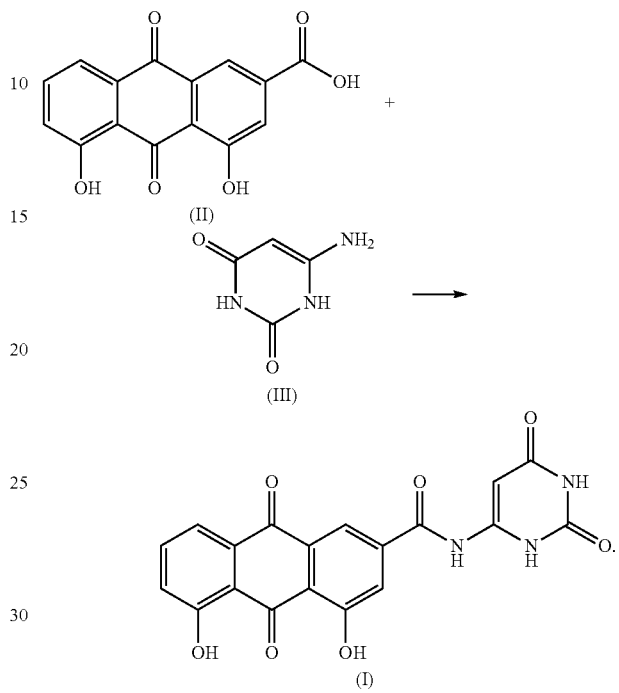

In another embodiment, the reaction of the compound of formula (II) with the compound of formula (III) includes the following steps: placing the compound of formula (II) and the compound of formula (III), in a molar ratio of 1:1 to 1:1.3, in a reactor; adding an organic solvent and a catalytic amount of EDC to obtain a reaction mixture; and heating the reaction mixture at 50-80° C. for 4-8 hours; and purifying the crude product on a silica gel fresh chromatography column with petroleum ether and ethyl acetate as an eluent to obtain the compound of formula (I).

In another embodiment, the organic solvent is toluene, tetrahydrofuran or acetonitrile.

In another embodiment, the organic solvent is acetonitrile.

In another embodiment, the molar ratio of the compound of formula (II) and the compound of formula (III) is 1:1.1.

In another embodiment, the reaction mixture is heated at 70° C.

In another embodiment, the reaction mixture is heated for 6 hours.

In another embodiment, the eluent is petroleum ether: ethyl acetate=3:10.

In another embodiment, the reaction of the compound of formula (II) with the compound of formula (III) includes the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 25-50° C. for 5-10 hours; placing the reaction mixture in a separating funnel to separate a crude product; purifying the crude product by recrystallization in methanol to obtain the compound of formula (I); and recycling the ionic liquid.

In another embodiment, the ionic liquid is 1-butyl-3-methylimidazolium tetrafluoroborate ([BMIM][BF$_4$]).

In another embodiment, the molar ratio of the compound of formula (II) and the compound of formula (III) is 1:1.1.

In another embodiment, the reaction mixture is heated at 30° C.

In another embodiment, the reaction mixture is heated for 8 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
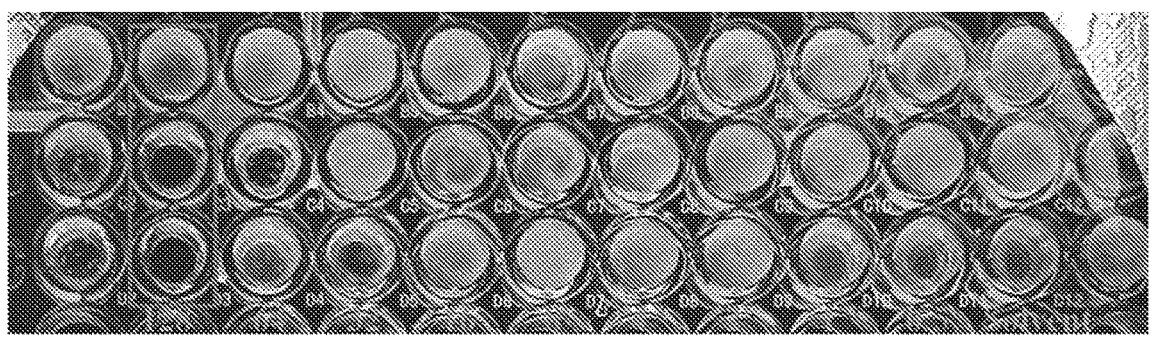
FIG. 1 shows the results of in vitro antibacterial activity of 6-aminouracil cassic acid ester against drug-resistant bacteria MDR-PA 18-174.

Reference will now be made in detail to embodiments of the present invention, example of which is illustrated in the accompanying drawings. The following examples illustrate the present invention, but the present invention is not limited to the following examples.

Example 1

Preparation of N-(2,6-dioxo-1,2,3,6-tetrahydropyrimidin-4-yl)-4,5-dihydroxy-9,10-dioxo-9,10-dihydroanthracene-2-carboxamide (Compound of Formula I)

In a 250 mL three-necked flask, 170.4 mg (0.6 mmol) of cassic acid and 115.0 mg (0.6 mmol) EDC (1-ethyl-3-(3-dimethylaminopropyl)carbodiimide) were dissolved in 90 mL of acetonitrile under nitrogen atmosphere. 83.8 mg (0.66 mmol) of 6-aminouracil was dissolved in 15 mL of acetonitrile, and slowly added dropwise to the flask by a separatory funnel. After the completion of the dropwise addition, the temperature was raised to 70° C., and the reaction was carried out for 6 hours. Thin layer chromatography was used to track the reaction to completion, heating was stopped, and the protective device was removed. The concentrated solution was washed with water, extracted with ethyl acetate, dried and concentrated to obtain a crude product. The crude product was further purified by silica gel column chromatography, with petroleum ether:ethyl acetate=3:10 as eluent, and the eluent was concentrated under reduced pressure and dried to obtain 169.4 mg of the title compound, a yield of 71.85%.

$^1$H-NMR (400 MHz, DMSO-d$_6$) δ (ppm): 11.91 (1H, s), 10.07 (1H, s), 8.15 (3H, d), 7.78 (1H, s), 7.07 (1H, d), 6.99 (1H, s), 6.83 (3H, s); $^{13}$C-NMR (400 MHz, DMSO-d$_6$) δ (ppm): 191.8, 181.4, 165.8, 161.9, 157.2, 138.5, 138.0, 134.3, 133.7, 124.6, 119.9, 116.9, 115.7.

Example 2

Preparation of Compound N-(2,6-dioxo-1,2,3,6-tetrahydropyrimidin-4-yl)-4,5-dihydroxy-9,10-dioxo-9,10-dihydroanthracene-2-carboxamide In a 250 mL three-necked flask, 170.4 mg (0.6 mmol) of cassic acid and 115.0 mg (0.6 mmol) EDC were dissolved in 90 mL of toluene under nitrogen atmosphere. 83.8 mg (0.66 mmol) of 6-aminouracil was dissolved in 15 mL of toluene, and slowly added dropwise to the flask by a separatory funnel. After the completion of the dropwise addition, the temperature was raised to 50° C., and the reaction was carried out for 8 hours. Thin layer chromatography was used to track the reaction to completion, heating was stopped, and the protective device was removed. The concentrated solution was washed with water, extracted with ethyl acetate, dried and concentrated to obtain a crude product. The crude product was further purified by silica gel column chromatography, with petroleum ether:ethyl acetate=3:10 as eluent, and the eluent was concentrated under reduced pressure and dried to obtain 161.6 mg of the title compound, a yield of 68.54%.

Example 3

Preparation of Compound N-(2,6-dioxo-1,2,3,6-tetrahydropyrimidin-4-yl)-4,5-dihydroxy-9,10-dioxo-9,10-dihydroanthracene-2-carboxamide In a 250 mL three-necked flask, 170.4 mg (0.6 mmol) of cassic acid and 115.0 mg (0.6 mmol) EDC were dissolved in 90 mL of tetrahydrofuran under nitrogen atmosphere. 83.8 mg (0.66 mmol) of 6-aminouracil was dissolved in 15 mL of tetrahydrofuran, and slowly added dropwise to the flask by a separatory funnel. After the completion of the dropwise addition, the temperature was raised to 80° C., and the reaction was carried out for 4 hours. Thin layer chromatography was used to track the reaction to completion, heating was stopped, and the protective device was removed. The concentrated solution was washed with water, extracted with ethyl acetate, dried and concentrated to obtain a crude product. The crude product was further purified by silica gel column chromatography, with petroleum ether:ethyl acetate=3:10 as eluent, and the eluent was concentrated under reduced pressure and dried to obtain 144.6 mg of the title compound, a yield of 61.32%.

Example 4

Preparation of Compound N-(2,6-dioxo-1,2,3,6-tetrahydropyrimidin-4-yl)-4,5-dihydroxy-9,10-dioxo-9,10-dihydroanthracene-2-carboxamide In a 250 mL three-necked flask, 170.4 mg (0.6 mmol) of cassic acid and 115.0 mg (0.6 mmol) EDC were dissolved in 90 mL of toluene under nitrogen atmosphere. 91.4 mg (0.72 mmol) of 6-aminouracil was dissolved in 15 mL of toluene, and slowly added dropwise to the flask by a separatory funnel. After the completion of the dropwise addition, the temperature was raised to 65° C., and the reaction was carried out for 6 hours. Thin layer chromatography was used to track the reaction to completion, heating was stopped, and the protective device was removed. The concentrated solution was washed with water, extracted with ethyl acetate, dried and concentrated to obtain a crude product. The crude product was further purified by silica gel column chromatography, with petroleum ether:ethyl acetate=3:10 as eluent, and the eluent was concentrated under reduced pressure and dried to obtain 158.3 mg of the title compound, a yield of 67.14%.

Example 5

Preparation of Compound N-(2,6-dioxo-1,2,3,6-tetrahydropyrimidin-4-yl)-4,5-dihydroxy-9,10-di-oxo-9,10-dihydroanthracene-2-carboxamide In a 250 mL three-necked flask, 170.4 mg (0.6 mmol) of cassic acid and 115.0 mg (0.6 mmol) EDC were dissolved in 90 mL of acetonitrile under nitrogen atmosphere. 91.4 mg (0.72 mmol) of 6-aminouracil was dissolved in 15 mL of acetonitrile, and slowly added dropwise to the flask by a separatory funnel. After the completion of the dropwise addition, the temperature was raised to 70° C., and the reaction was carried out for 7 hours. Thin layer chromatography was used to track the reaction to completion, heating was stopped, and the protective device was removed. The concentrated solution was washed with water, extracted with ethyl acetate, dried and concentrated to obtain a crude product. The crude product was further purified by silica gel column chromatography, with petroleum ether:ethyl acetate=3:10 as eluent, and the eluent was concentrated under reduced pressure and dried to obtain 145.2 mg of the title compound, a yield of 61.56%.

Example 6

Preparation of Compound N-(2,6-dioxo-1,2,3,6-tetrahydropyrimidin-4-yl)-4,5-dihydroxy-9,10-di-oxo-9,10-dihydroanthracene-2-carboxamide In a 250 mL three-necked flask, 170.4 mg (0.6 mmol) of cassic acid and 115.0 mg (0.6 mmol) EDC were dissolved in 90 mL of tetrahydrofuran under nitrogen atmosphere. 83.8 mg (0.66 mmol) of 6-aminouracil was dissolved in 15 mL of tetrahydrofuran, and slowly added dropwise to the flask by a separatory funnel. After the completion of the dropwise addition, the temperature was raised to 60° C., and the reaction was carried out for 5 hours. Thin layer chromatography was used to track the reaction to completion, heating was stopped, and the protective device was removed. The concentrated solution was washed with water, extracted with ethyl acetate, dried and concentrated to obtain a crude product. The crude product was further purified by silica gel column chromatography, with petroleum ether:ethyl acetate=3:10 as eluent, and the eluent was concentrated under reduced pressure and dried to obtain 154.1 mg of the title compound, a yield of 65.33%.

Example 7

Preparation of Compound N-(2,6-dioxo-1,2,3,6-tetrahydropyrimidin-4-yl)-4,5-dihydroxy-9,10-di-oxo-9,10-dihydroanthracene-2-carboxamide In a 250 mL three-necked flask, 170.4 mg (0.6 mmol) of cassic acid, 83.8 mg (0.66 mmol) of 6-aminouracil and 10.3 mg (0.006 mmol) silicomolybdic acid were dissolved in 100 mL of 1-butyl-3-methylimidazolium tetrafluoroborate under nitrogen atmosphere. After full dissolution, the temperature was raised to 30° C. and the reaction was carried out for 8 hours. Thin layer chromatography was used to track the reaction to completion, heating was stopped, and the protective device was removed. The reaction mixture system was allowed to separate into layers to give a crude product. The crude product was recrystallized with 40 mL methanol and dried to obtain 195.2 mg of the title compound, a yield of 82.79%.

Example 8

Preparation of Compound N-(2,6-dioxo-1,2,3,6-tetrahydropyrimidin-4-yl)-4,5-dihydroxy-9,10-di-oxo-9,10-dihydroanthracene-2-carboxamide In a 250 mL three-necked flask, 170.4 mg (0.6 mmol) of cassic acid, 83.8 mg (0.66 mmol) of 6-aminouracil and 10.3 mg (0.006 mmol) silicomolybdic acid were dissolved in 100 mL of 1-butyl-3-methylimidazolium tetrafluoroborate under nitrogen atmosphere. After full dissolution, the temperature was raised to 50° C. and the reaction was carried out for 5 hours. Thin layer chromatography was used to track the reaction to completion, heating was stopped, and the protective device was removed. The reaction mixture system was allowed to separate into layers to give a crude product. The crude product was recrystallized with 40 mL methanol and dried to obtain 183.6 mg of the title compound, a yield of 77.85%.

Example 9

Antibacterial Activity Test of the Compounds of the Invention

The minimal inhibitory concentration (MIC) of the compounds as determined by a microbroth dilution method with gentamicin, cefazolin sodium and ceftriaxone sodium as positive control.

The experimental strains included methicillin-resistant Gram-positive bacteria: methicillin-resistant *Staphylococcus aureus* MRSA 18-222, 18-575; multiple drug-resistant Gram-negative bacteria: vancomycin-resistant enterococci VRE 18-80, 18-94; multidrug-resistant *Pseudomonas aeruginosa* MDR-PA 18-1774, 18-202; carbapenem-resistant *Acinetobacter baumannii* CR-AB 18-183, 18-560. All the experimental strains were donated by Huashan Hospital affiliated to Fudan University (Institute of Antibiotics, Fudan University) and used after routine identification.

Preparation of Test Strains:

Preparation of MHB medium: 20.0 g MHB medium was added to 1 L distilled water, boiled until completely dissolved, packed in conical bottles and sterilized at 121° C. for 15 min.

The experimental strain was cultured to the logarithmic growth phase: under aseptic condition, the experimental strain was inoculated into 100 mL NMB medium and incubated in a constant temperature and humidity incubator at 37° C. for 20-22 hours.

Preparation of storage solution: weigh the sample to be tested, dissolve it with 1% DMSO solution, prepare a storage solution with a concentration of 2560 μg/mL, weigh a positive reference substance, dissolve it with aseptic distilled water, and configure a storage solution with a concentration of 2560 μg/mL.

Preparation of bacterial suspension: under aseptic condition, the experimental strains cultured to logarithmic growth phase were adjusted to 0.5 MCF turbidity standard with MHB medium and diluted according to 1:10, and the bacterial suspension with concentration of $10^6$ CFU/mL was prepared for standby.

Dilution of storage solution and inoculation of experimental strain: under aseptic condition, the storage solution was diluted to 256 μg/mL solution. Take a sterile 96-well plate, add 200 μL MHB medium to the 12th well, and add 100 μL MHB medium to each well. Add 100 μL of positive control solution to the first well, mix well, and suck 100 μL from it and discard. Add 100 μL of the compound sample solution to the second well, mix well, and then pipette 100 μL to the third well. After mixing, pipette 100 μL to the fourth well, and dilute to the 11th well in this way. Finally, 100 μL was pipetted from the 11th well and discarded. The 12th hole was the growth control without drugs. So far, the concentration of the positive reference substance is 128 μg/mL, the concentrations of the sample solution are 128, 64, 16, 8, 4, 2, 1, 0.5, 0.25 μg/mL respectively. Then, 100 μL of the prepared bacterial suspension is added to each well, so that the final concentration of the bacterial liquid in each well is $5 \times 10^5$ CFU/mL.

Incubation: Cover the 96-well plate inoculated with the experimental strains, and incubate in a constant temperature and humidity box at 37° C. for 20-22 hours.

Interpretation of the MIC endpoint: The concentration that can completely inhibit the growth of bacteria in a 96-well plate under a black background is the lowest inhibitory concentration of the sample against the bacteria.

Figure 2:
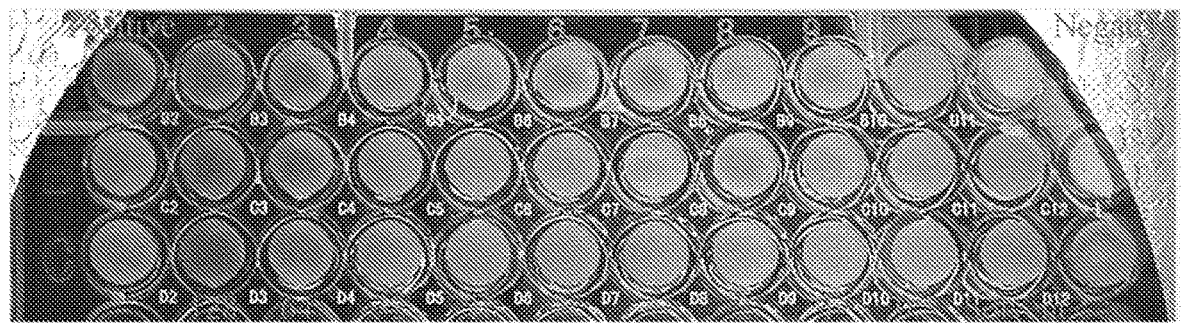
FIG. 2 shows the results of in vitro antibacterial activity of cassic acid against drug-resistant bacteria MDR-PA 18-174.
Figure 3:
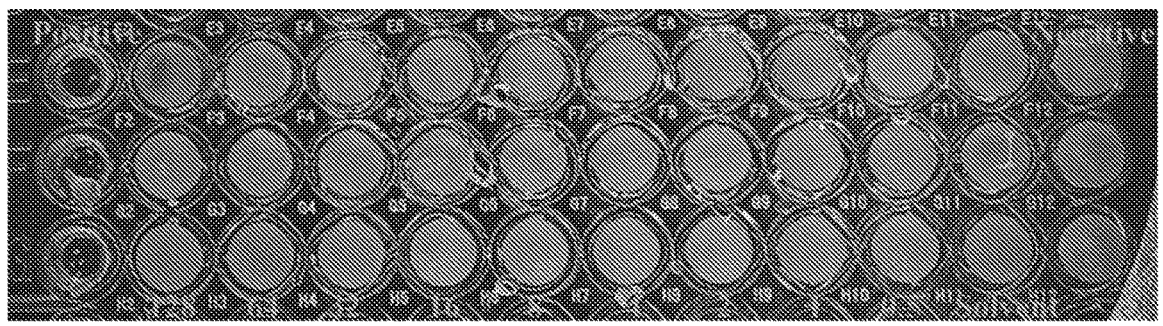
FIG. 3 shows the results of in vitro antibacterial activity of 6-aminouracil against drug-resistant bacteria MDR-PA 18-174.
Figure 4:
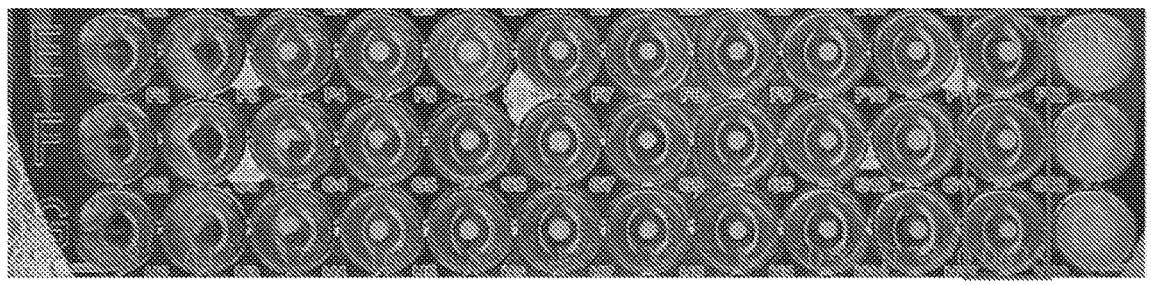
FIG. 4 shows the results of in vitro antibacterial activity of gentamicin against drug-resistant bacteria MDR-PA 18-174.
Figure 5:
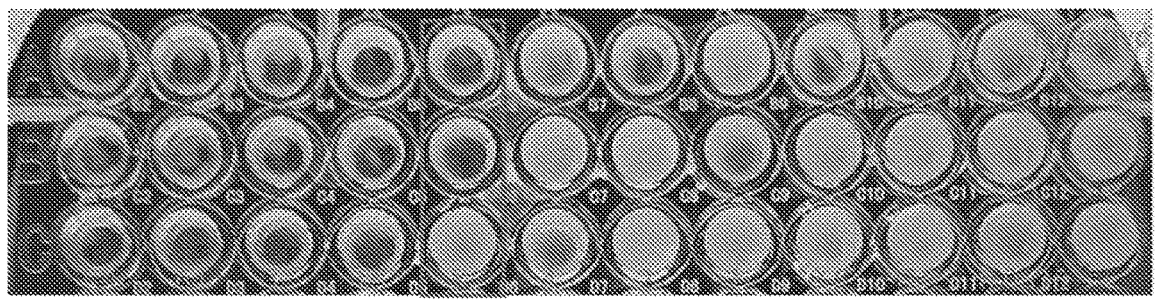
FIG. 5 shows the results of in vitro antibacterial activity of cefazolin sodium against drug-resistant bacteria MDR-PA 18-174.
Figure 6:
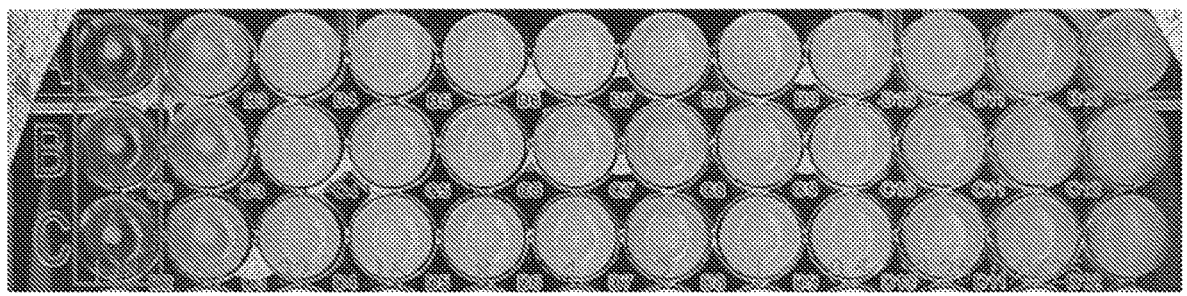
FIG. 6 shows the results of in vitro antibacterial activity of ceftriaxone sodium against drug-resistant bacteria MDR-PA 18-174.

In FIGS. 1-6, the twelve wells represent twelve groups, from left to right, positive, 128 μg/mL, 64 μg/mL, 32 μg/mL, 16 μg/mL, 8 μg/mL, 4 μg/mL, 2 μg/mL, 1 μg/mL, 0.25 μg/mL, 0.0625 μg/mL, Negative. FIG. 1 shows the in vitro antibacterial activity of rhein 6-Aminouracil derivative against drug-resistant bacteria MDR-PA 18-174. FIG. 2 shows the in vitro antibacterial activity of rhein against drug-resistant bacteria MDR-PA 18-174. FIG. 3 shows the in vitro antibacterial activity of 6-Aminouracil against drug-resistant bacteria MDR-PA 18-174. FIG. 4 shows the in vitro antibacterial activity of gentamicin against drug-resistant bacteria MDR-PA 18-174. FIG. 5 shows the in vitro antibacterial activity of cefazolin sodium against drug-resistant bacteria MDR-PA 18-174. FIG. 6 shows the in vitro antibacterial activity of ceftriaxone sodium against drug-resistant bacteria MDR-PA 18-174. The results are shown in Table 1.

According to the experimental results of FIGS. 1-6 and Table 1, cassic acid and 6-aminouracil had no inhibitory effect on drug-resistant bacteria, while 6-aminouracil cassic acid ester showed a strong inhibitory effect on multi-drug resistant *Pseudomonas aeruginosa* MDR-PA (MIC=128 μg/mL) as well as vancomycin resistant *Enterococcus* VRE (MIC=64 μg/mL). In summary, the 6-aminouracil cassic acid ester of the present invention can be used as an antibacterial drug candidate for multi-drug resistant *Pseudomonas aeruginosa* of gram-negative bacteria, and further pre-clinical research.

What is claimed is:

1. A compound of the following formula (I):

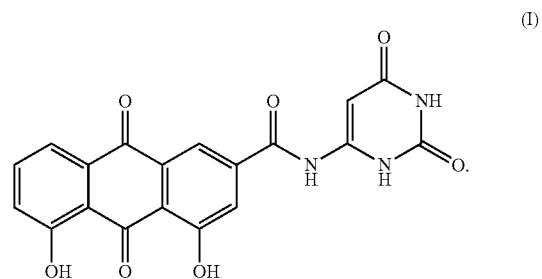 [SMILES: O=C(Nc1cc(=O)[nH]c(=O)[nH]1)c1cc(O)c2c(c1)C(=O)c1cccc(O)c1C2=O]

2. A method of preparing the compound of formula (I) of claim 1, comprising: reacting a compound of formula (II) with a compound of formula (III) to obtain the compound of formula (I):

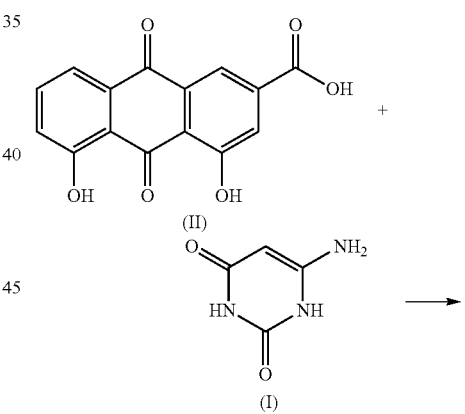

TABLE 1

Minimum bacteriostatic concentration of test drug and positive drug (μg · mL$^{-1}$)

| | Strain | | | | | | | |
|---|---|---|---|---|---|---|---|---|
| | MRSA | | VRE | | MDR-PA | | CR-AB | |
| Sample | 18-222 | 18-575 | 18-80 | 18-94 | 18-174 | 18-202 | 18-183 | 18-560 |
| 6-Aminouracil cassic acid ester | >128 | >128 | >128 | 64 | 128 | >128 | >128 | >128 |
| Gentamicin | 128 | 2 | 0.0625 | >128 | 0.0625 | 0.0625 | >128 | >128 |
| Cefazolin sodium | >128 | >128 | 32 | >128 | 8 | 128 | >128 | >128 |
| Ceftriaxone sodium | >128 | >128 | 8 | >128 | 128 | 16 | >128 | >128 |
| Cassic acid | >128 | >128 | >128 | >128 | >128 | >128 | >128 | >128 |
| 6-Aminouracil | >128 | >128 | >128 | >128 | >128 | >128 | >128 | >128 |

-continued

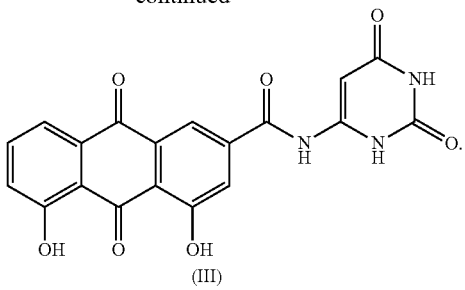

(III)

3. The method of claim 2, wherein the reaction of the compound of formula (II) with the compound of formula (III) comprises the following steps:
placing the compound of formula (II) and the compound of formula (III), in a molar ratio of 1:1 to 1:1.3, in a reactor;
adding an organic solvent and a catalytic amount of EDC under nitrogen atmosphere to obtain a reaction mixture; and
heating the reaction mixture at 50-80° C. for 4-8 hours;
concentrating the reaction mixture and extracting the reaction mixture with ethyl acetate to obtain a crude product; and
purifying the crude product on a silica gel fresh chromatography column with petroleum ether and ethyl acetate as an eluent to obtain the compound of formula (I).

4. The method of claim 3, wherein the organic solvent is toluene, tetrahydrofuran or acetonitrile.

5. The method of claim 4, wherein the organic solvent is acetonitrile.

6. The method of claim 3, wherein the molar ratio of the compound of formula (II) and the compound of formula (III) is 1:1.1.

7. The method of claim 3, wherein the reaction mixture is heated at 70° C.

8. The method of claim 3, wherein the reaction mixture is heated for 6 hours.

9. The method of claim 3, wherein the eluent is petroleum ether:ethyl acetate=3:10.

10. The method of claim 2, wherein the reaction of the compound of formula (II) with the compound of formula (III) comprises the following steps:
placing the compound of formula (II), a catalyst, and an ionic liquid in a reactor under nitrogen atmosphere, the catalyst being 12-molybdosilicic acid hydrate ($H_6Mo_{12}O_{41}Si$);
adding the compound of formula (III) to the reactor to form a reaction mixture;
heating the reaction mixture at 25-50° C. for 5-10 hours;
placing the reaction mixture in a separating funnel to separate a crude product;
purifying the crude product by recrystallization in methanol to obtain the compound of formula (I); and
recycling the ionic liquid.

11. The method of claim 10, wherein the ionic liquid is 1-butyl-3-methylimidazolium tetrafluoroborate ([BMIM][$BF_4$]).

12. The method of claim 10, wherein the compound of formula (II) and the compound (III) have a molar ratio of 1:1 to 1:1.3.

13. The method of claim 12, wherein the molar ratio of the compound of formula (II) and the compound of formula (III) is 1:1.1.

14. The method of claim 10, wherein the reaction mixture is heated at 30° C.

15. The method of claim 10, wherein the reaction mixture is heated for 8 hours.

* * * * *